United States Patent
Burki et al.

(10) Patent No.: US 9,901,333 B2
(45) Date of Patent: Feb. 27, 2018

(54) SOFT TISSUE FIXATION SYSTEM

(71) Applicant: DePuy Synthes Products, Inc., Raynham, MA (US)

(72) Inventors: Patrick Burki, Solothurn (CH); Nicolas Bouduban, Solothurn (CH); Dieter Schmidli, Seewen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 633 days.

(21) Appl. No.: 13/832,201

(22) Filed: Mar. 15, 2013

(65) Prior Publication Data

US 2014/0277127 A1 Sep. 18, 2014

Related U.S. Application Data

(63) Continuation-in-part of application No. 13/800,868, filed on Mar. 13, 2013.

(60) Provisional application No. 61/780,077, filed on Mar. 13, 2013.

(51) Int. Cl.
*A61B 17/04* (2006.01)

(52) U.S. Cl.
CPC .... *A61B 17/0401* (2013.01); *A61B 2017/042* (2013.01); *A61B 2017/0403* (2013.01); *A61B 2017/0409* (2013.01); *A61B 2017/0438* (2013.01); *A61B 2017/0454* (2013.01)

(58) Field of Classification Search
CPC .............. A61B 17/0401; A61B 17/864; A61B 17/8625; A61B 2017/0409; A61B 2017/042; A61B 2017/0438; A61B 2017/0445; A61B 2017/0446; A61B 2017/0454; A61B 2017/0458; A61B 2017/0414; A61B 2017/0448; A61B 2017/045; A61B 2017/0456; A61F 2/0811; A61F 2/0817; A61F 2/0835
See application file for complete search history.

(56) References Cited

U.S. PATENT DOCUMENTS

| 5,733,307 A | * | 3/1998 | Dinsdale | ............ | A61B 17/0401 |
| | | | | | 606/104 |
| 6,056,751 A | | 5/2000 | Fenton | | |
| 6,508,830 B2 | | 1/2003 | Steiner | | |

(Continued)

FOREIGN PATENT DOCUMENTS

| CN | 101056587 A | 10/2007 |
| CN | 101933826 A | 1/2011 |

(Continued)

*Primary Examiner* — Christopher L Templeton
(74) *Attorney, Agent, or Firm* — Baker & Hostetler LLP

(57) ABSTRACT

A soft tissue fixation assembly includes a plurality of deformable bone anchors and a suture that is configured to fixedly attach to each of the bone anchors. One or more of the bone anchors can be inserted into a bone, and one or more of the bone anchors can be inserted through soft tissue and into the bone. The suture can be inserted through the bone anchors, and energy can be applied to the anchors, thereby causing a deformable material of the bone anchors to deform, thereby capturing the strand of suture in the bone anchor. The strand of suture can be placed in tension, and can extend over the soft tissue so as to retain the soft tissue in contact with the bone.

27 Claims, 12 Drawing Sheets

(56) References Cited

U.S. PATENT DOCUMENTS

| | | | |
|---|---|---|---|
| 6,652,560 B1* | 11/2003 | Gerke | A61F 2/0811 606/232 |
| 7,491,217 B1 | 2/2009 | Hendren et al. | |
| 8,317,825 B2 | 11/2012 | Stone | |
| 2002/0161401 A1* | 10/2002 | Steiner | A61B 17/0401 606/232 |
| 2003/0041426 A1 | 3/2003 | Genova et al. | |
| 2004/0068267 A1 | 4/2004 | Harvie et al. | |
| 2004/0236374 A1 | 11/2004 | Bonutti et al. | |
| 2005/0245932 A1* | 11/2005 | Fanton | A61B 17/0401 606/232 |
| 2006/0004364 A1 | 1/2006 | Green et al. | |
| 2006/0095130 A1* | 5/2006 | Caborn | A61F 2/0811 623/13.14 |
| 2006/0106422 A1 | 5/2006 | Del et al. | |
| 2006/0189993 A1* | 8/2006 | Stone | A61B 17/0401 604/506 |
| 2007/0055255 A1* | 3/2007 | Siegel | A61F 2/0811 606/232 |
| 2007/0142835 A1 | 6/2007 | Green et al. | |
| 2007/0167950 A1 | 7/2007 | Tauro et al. | |
| 2007/0198017 A1* | 8/2007 | Tschakaloff | A61B 17/0401 606/326 |
| 2007/0288023 A1 | 12/2007 | Pellegrino | |
| 2008/0109038 A1* | 5/2008 | Steiner | A61B 17/0401 606/232 |
| 2008/0125815 A1* | 5/2008 | Heaven | A61B 17/0401 606/308 |
| 2008/0161806 A1* | 7/2008 | Donnelly | A61F 2/0811 606/60 |
| 2008/0269743 A1 | 10/2008 | McNamara et al. | |
| 2008/0287992 A1 | 11/2008 | Tornier et al. | |
| 2009/0018581 A1* | 1/2009 | Anderson | A61B 17/0401 606/232 |
| 2009/0043342 A1* | 2/2009 | Freedland | A61B 17/0401 606/313 |
| 2009/0069823 A1 | 3/2009 | Foerster et al. | |
| 2009/0317768 A1 | 12/2009 | Mayer et al. | |
| 2009/0318960 A1 | 12/2009 | Burkhart | |
| 2010/0241229 A1 | 9/2010 | Baehre et al. | |
| 2010/0274356 A1* | 10/2010 | Fening | A61F 2/0811 623/13.14 |
| 2011/0009885 A1* | 1/2011 | Graf | A61B 17/0401 606/151 |
| 2011/0046670 A1 | 2/2011 | Lehmann et al. | |
| 2011/0062617 A1 | 3/2011 | Lehmann | |
| 2011/0270308 A1 | 11/2011 | Kilburn-Peterson et al. | |
| 2012/0022588 A1 | 1/2012 | Berg | |
| 2012/0078300 A1 | 3/2012 | Mayer et al. | |
| 2012/0095506 A1* | 4/2012 | Mayer | A61B 17/0401 606/232 |
| 2012/0129131 A1 | 5/2012 | Baehre et al. | |
| 2012/0130422 A1 | 5/2012 | Hootstein | |
| 2012/0197296 A1* | 8/2012 | Mayer | A61B 17/0401 606/232 |
| 2012/0197316 A1* | 8/2012 | Mayer | A61B 17/0401 606/328 |
| 2013/0267999 A1 | 10/2013 | Ng et al. | |
| 2014/0005721 A1 | 1/2014 | Mayer | |
| 2014/0309691 A1* | 10/2014 | Brown | A61L 31/06 606/232 |

FOREIGN PATENT DOCUMENTS

| | | |
|---|---|---|
| WO | WO 2009/003294 | 1/2009 |
| WO | WO 2009/036576 | 3/2009 |
| WO | WO 2009/055952 A1 | 5/2009 |
| WO | WO 2012/100358 A1 | 8/2012 |
| WO | WO 2012/100359 A1 | 8/2012 |

* cited by examiner

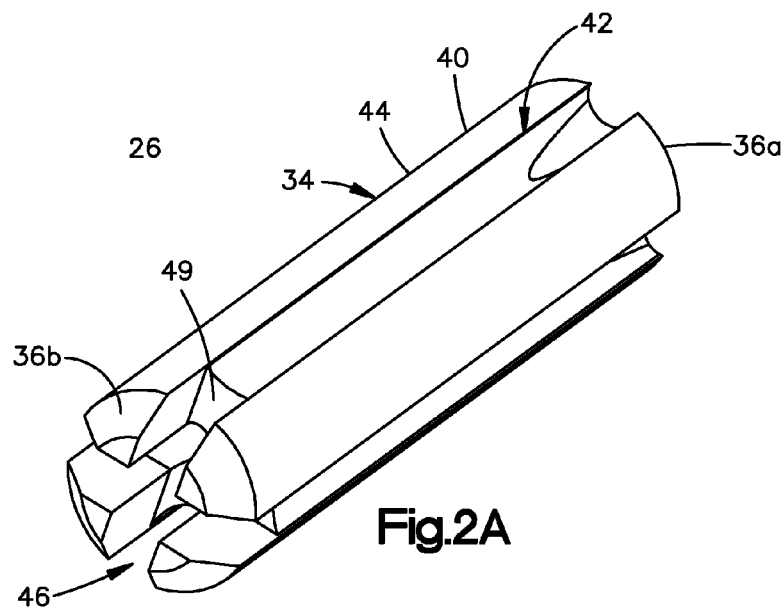
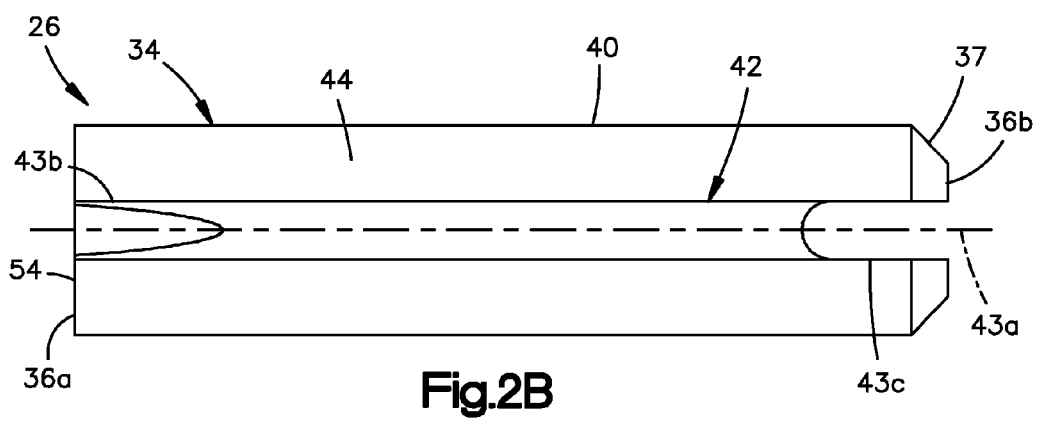
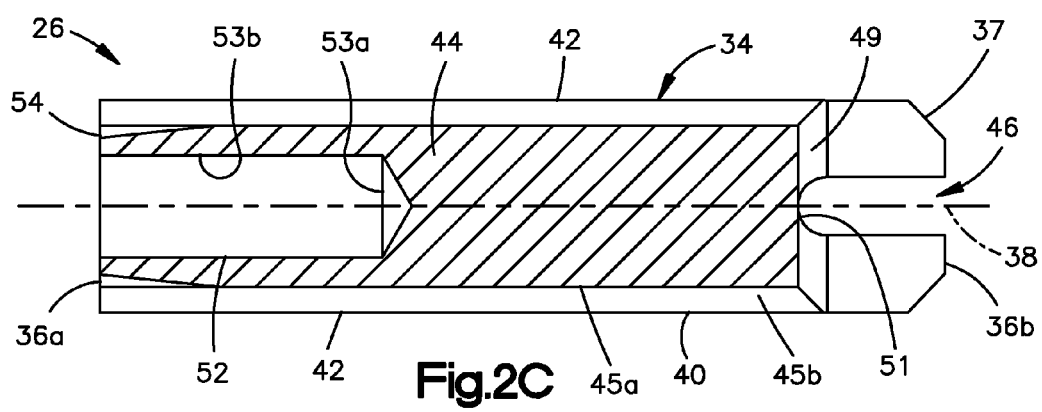

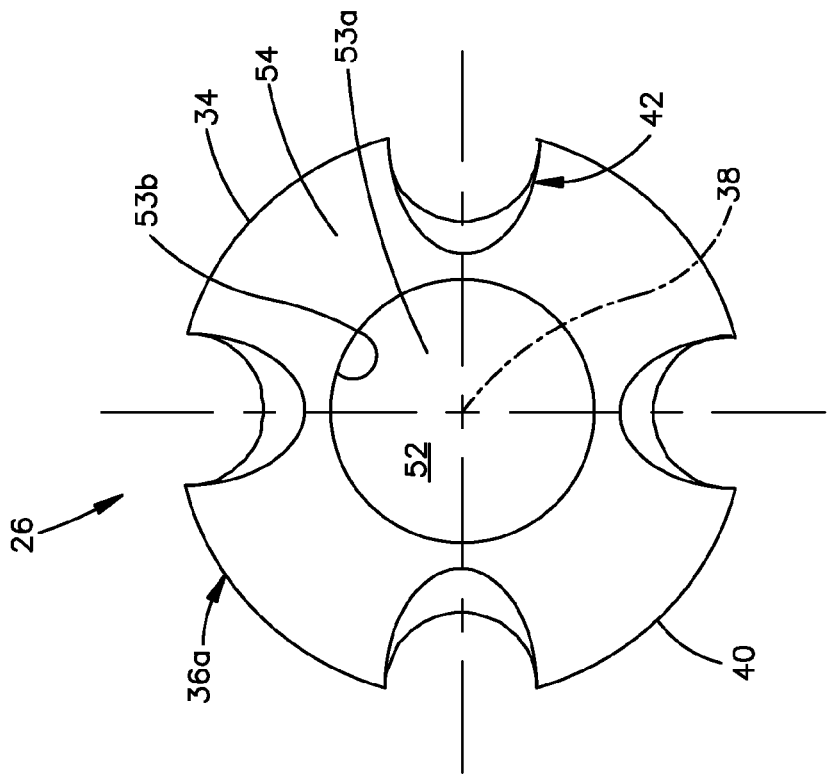
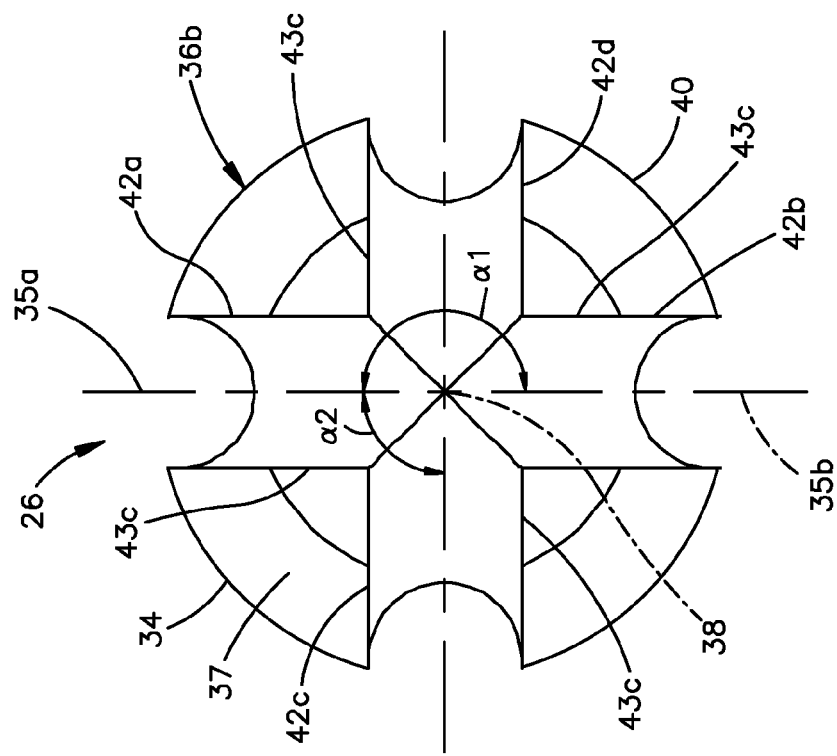
Fig.2E
Fig.2D

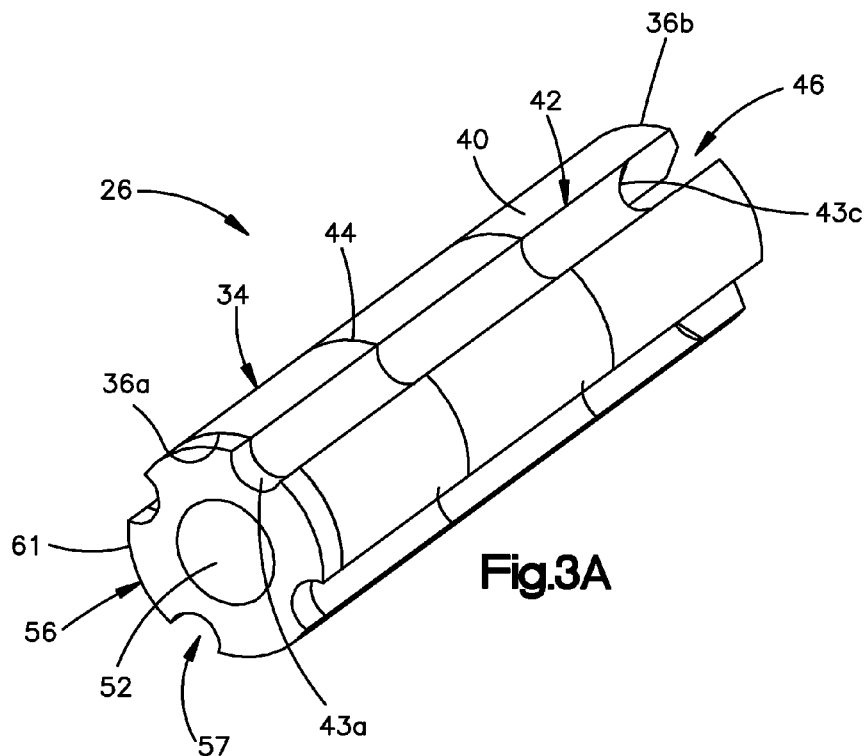
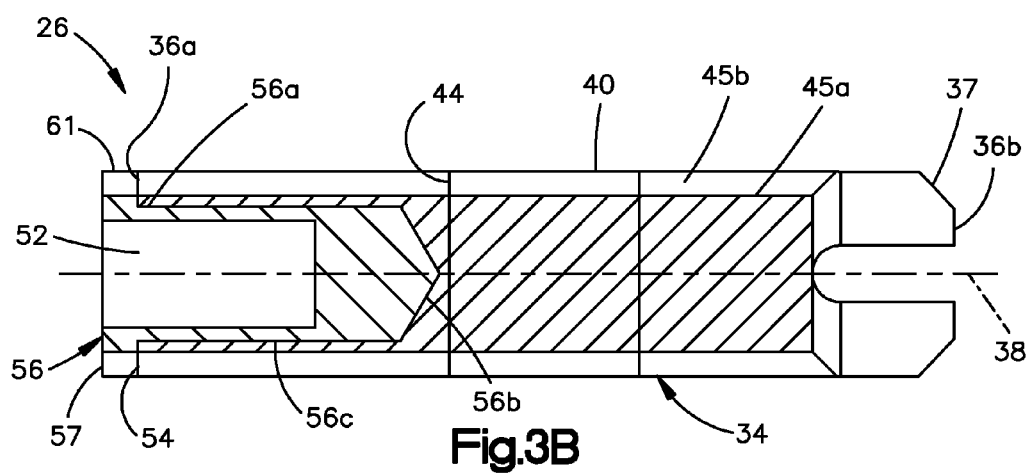

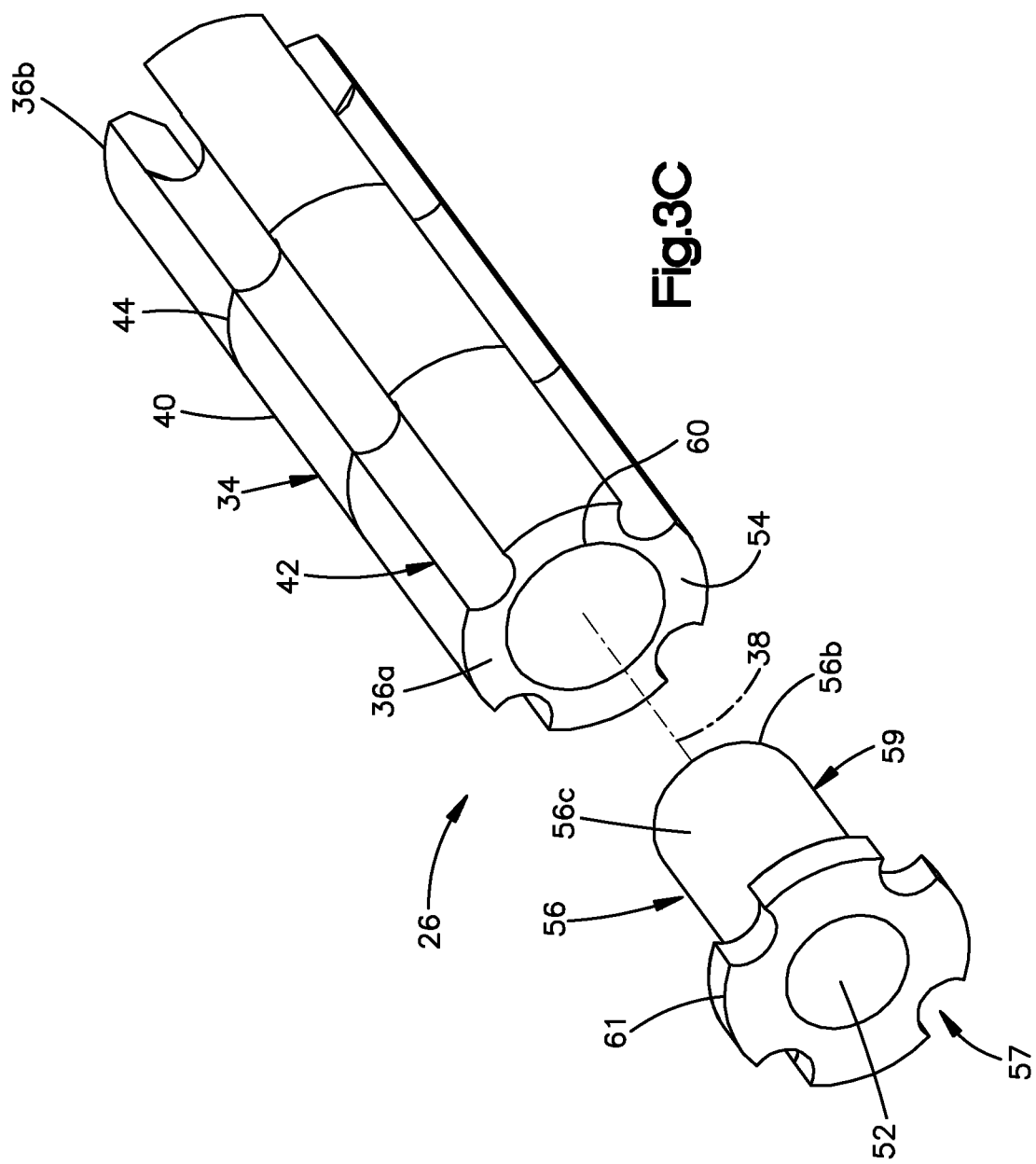

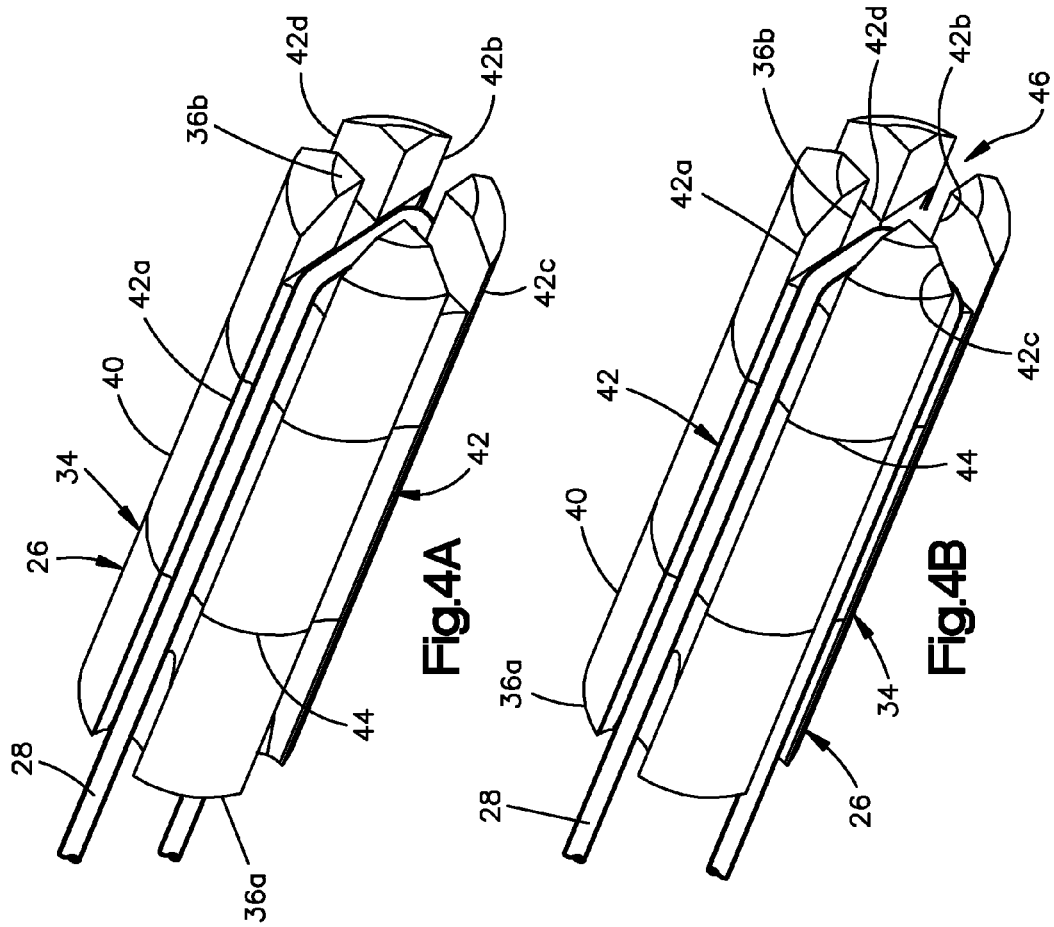

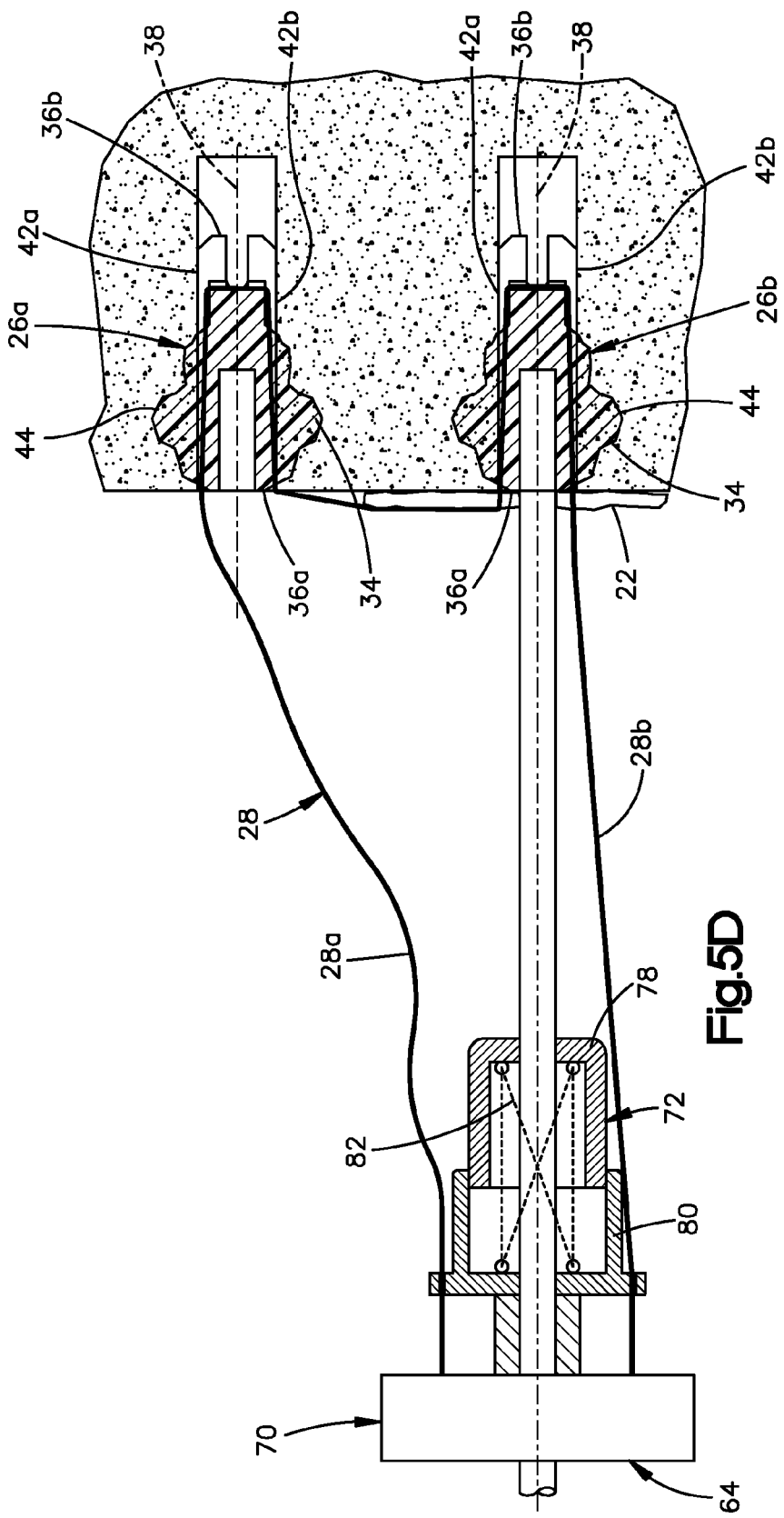

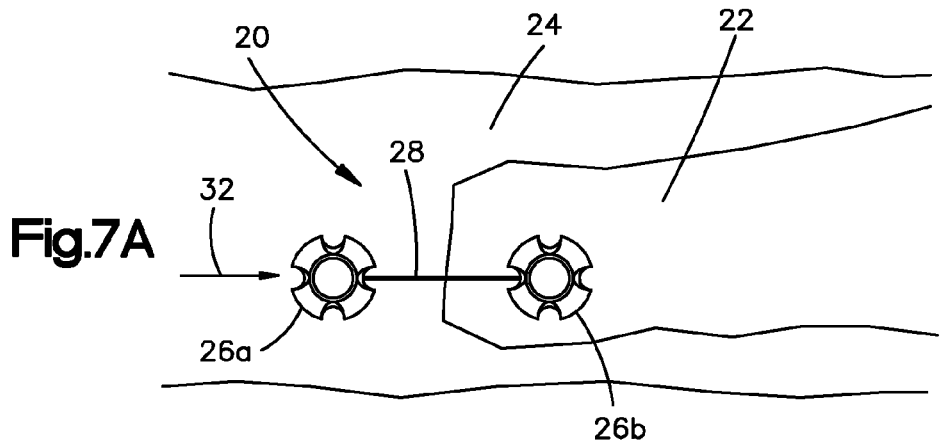
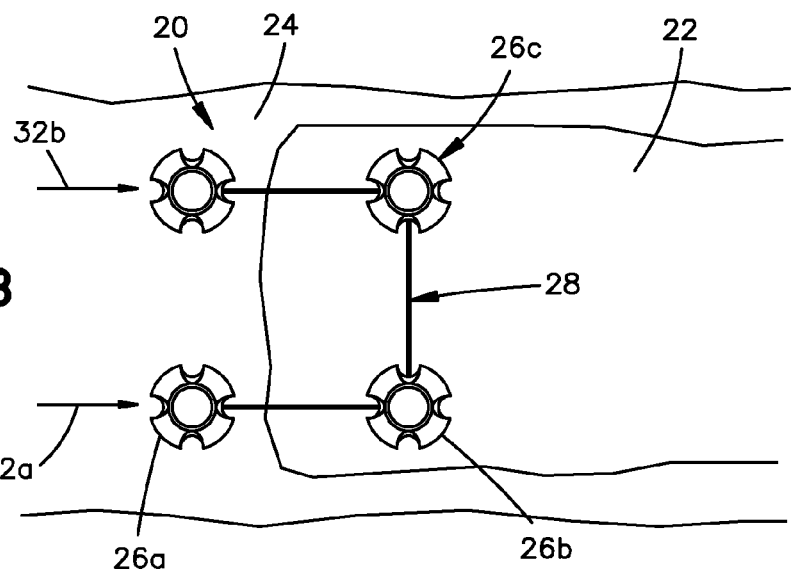
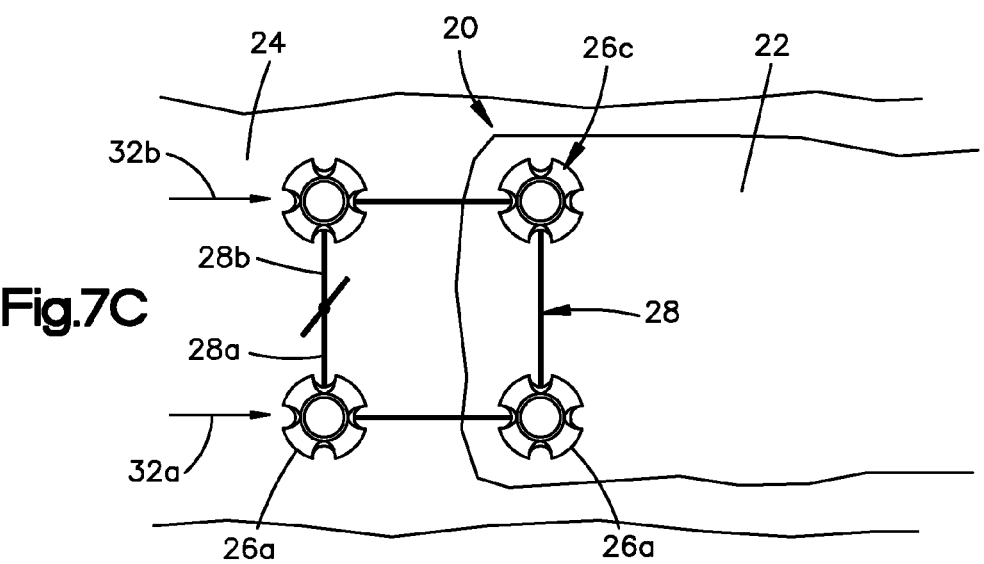

SOFT TISSUE FIXATION SYSTEM

CROSS-REFERENCE TO RELATED APPLICATIONS

This is a continuation-in-part of U.S. patent application Ser. No. 13/800,868, filed Mar. 13, 2013, the disclosure of which is incorporated by reference as if set forth in its entirety herein. This claims the benefit of U.S. Patent Application Ser. No. 61/780,077 filed Mar. 13, 2013, the disclosure of which is hereby incorporated by reference as if set forth in its entirety herein.

BACKGROUND

Common injuries can involve tears of soft tissue, such as tendons and ligaments, and detachments of soft tissue from one or more underlying bones. As one example, the tendons at the ends of the rotator cuff muscles can become torn, leading to pain and restricted movement of the musculoskeletal system. The soft tissue can be conventionally re-attached to bone arthroscopically, for instance by driving bone anchors into the bone at a desired locations, and attaching separate strands of suture to each of the bone anchors and the soft tissue. Each of the separate strands of suture is then tied off to draw the soft tissue against the bone, thereby allowing reattachment of the soft tissue to the bone.

What is desired is an improved method and apparatus for attaching soft tissue to bone.

SUMMARY

In accordance with one embodiment, a bone anchor includes a bone anchor body defining a proximal end, a distal end that is spaced from the proximal end along a longitudinal axis, and a perimeter that extends between the proximal end and the distal end. The bone anchor body is configured to receive a strand of suture. At least a portion of the bone anchor body comprises a deformation material that is responsive to an applied energy so as to deform and, when the strand of suture is received by the anchor body, capture the strand of suture with respect to movement relative to the bone anchor body.

BRIEF DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and instrumentalities shown. In the drawings:

FIG. 2A is a perspective view of a bone anchor of the soft tissue fixation assembly illustrated in FIG. 1, showing the bone anchor in accordance with one embodiment;

FIG. 2B is a side elevation view of the bone anchor illustrated in FIG. 2A;

FIG. 2C is a sectional side elevation view of the bone anchor illustrated in FIG. 2A;

FIG. 2D is a bottom plan view of the bone anchor illustrated in FIG. 2A;

FIG. 2E is a top plan view of the bone anchor illustrated in FIG. 2A;

FIG. 3A is a perspective view of a bone anchor constructed in accordance with an alternative embodiment;

FIG. 3B is a sectional side elevation view of the bone anchor illustrated in FIG. 3A;

FIG. 3C is an exploded perspective view of the bone anchor illustrated in FIG. 3A;

FIG. 4A is a perspective view of a suture extending through opposed channels of the bone fixation element illustrated in FIG. 2A;

FIG. 4B is a perspective view of a suture extending through adjacent channels of the bone fixation element illustrated in FIG. 2A;

FIG. 5D is a schematic sectional side elevation view of the soft tissue fixation system illustrated in FIG. 5C, shown after activation of the actuation assembly;

FIG. 7A is a schematic plan view of the soft tissue fixation assembly as illustrated in FIG. 1, but showing the bone anchors in one arrangement;

FIG. 7B is a schematic plan view of the soft tissue fixation assembly as illustrated in FIG. 7A, but showing the bone anchors in another arrangement as illustrated in FIG. 1, shown as an open arrangement;

FIG. 7C is a schematic plan view of the soft tissue fixation assembly as illustrated in FIG. 7B, but showing the bone anchors in a closed arrangement in accordance with one embodiment;

DETAILED DESCRIPTION

Figure 1:
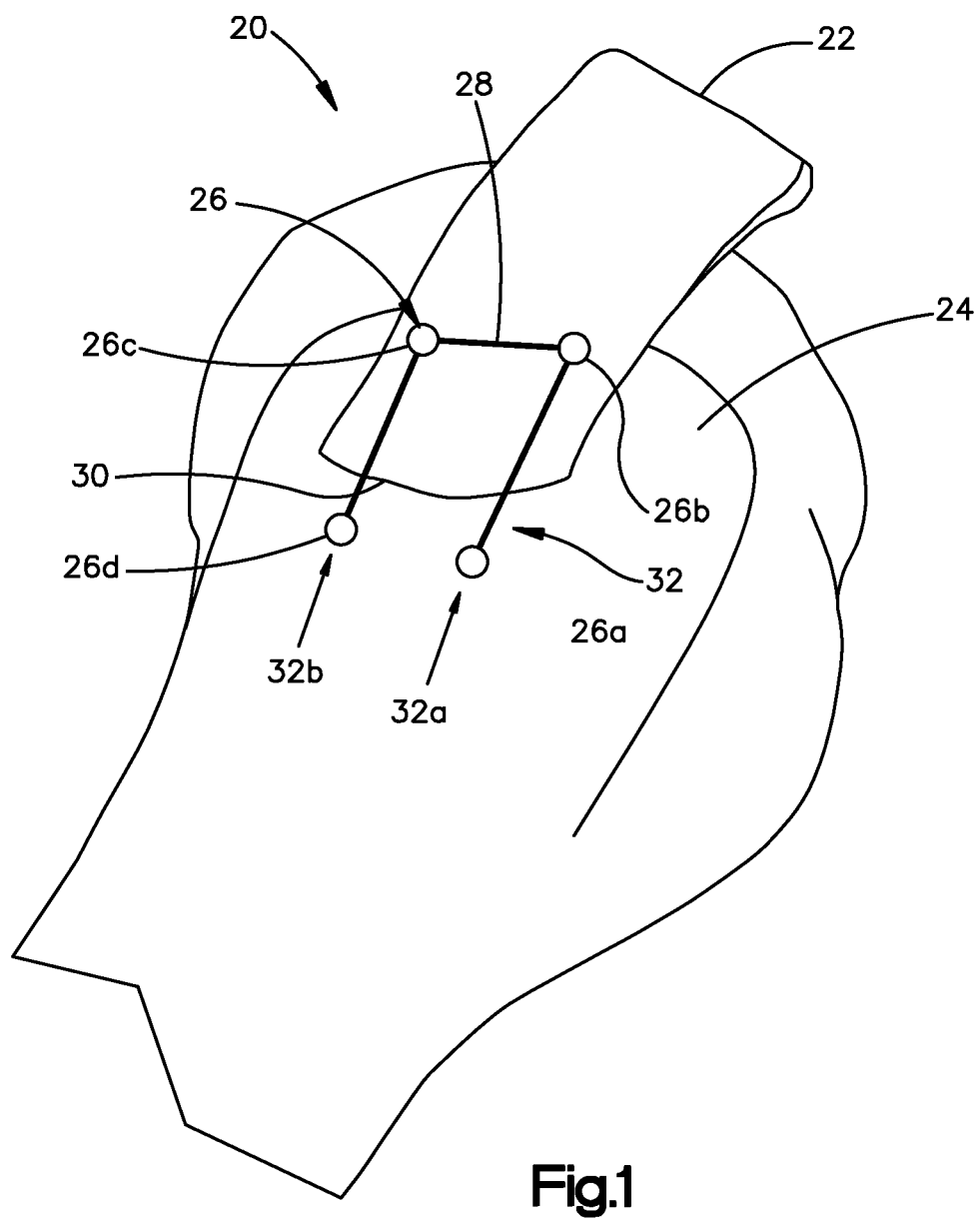
FIG. 1 is a schematic top plan view of a soft tissue fixation assembly anchored to bone and retaining a soft tissue against the bone, the soft tissue fixation assembly constructed in accordance with one embodiment.

Referring initially to FIGS. 1 and 8B, a soft tissue fixation assembly 20 is configured to secure a soft tissue 22 against a surface of an underlying bone 24 so as to promote attachment of the soft tissue 22 to the bone 24. The soft tissue 22 can be detached from the bone due to an anatomical defect, trauma, or the like, and can be configured as any anatomical soft tissue in the human or other animal body, such as a tendon or ligament. For instance, in accordance with one embodiment, the tendon can be a rotator cuff tendon or any other tendon as desired.

The fixation assembly 20 can include at least one bone anchor 26, such as first and second bone anchors 26a and 26b, respectively, and a strand of suture 28 that is configured to attach to each of the bone anchors 26a and 26b. For instance, the strand of suture 28 is configured to be received by each of the bone anchors 26 and 26b. The first bone and second bone anchors 26a and 26b can, for instance, be driven into the bone 24, such that the strand of suture 28 extends from the first bone anchor 26a to the second bone anchor 26b. One of the first and second bone anchors 26a and 26b, for instance the second bone anchor 26b as illustrated, can be driven through the soft tissue 22 and into the bone 24, referred to as a trans-tendon technique. The other of the first and second bone anchors 26a and 26b, for instance the first one anchor 26a as illustrated, can be driven into the bone 24 at a location spaced from the soft tissue 22. Thus, the strand of suture 28 can extend from the first bone anchor 26a along an outer surface of the bone 24, across an interface 30 between the bone 24 and the soft tissue 22, to the second bone anchor 26b. The strand of suture 28 can be under tension between the first and second bone anchors 26a and 26b so as to apply a force against the soft tissue soft 22 toward the bone 24, thereby causing the soft tissue 22 to maintain contact with the bone 24. It should be recognized that in most instances it may not be recommended, during rotator cuff repair, to insert the bone anchors 26 in the intraarticular space of the shoulder, but rather to position the bone anchors about the joint.

It will be appreciated from the description below that the fixation assembly 20 can include any number of bone anchors 26, such as a plurality of bone anchors 26, as desired. One or more of the plurality of bone anchors 26 can be driven through the soft tissue 22 and into the bone 24. One or more others of the plurality of bone anchors can be driven into the bone 24 at a location spaced from the soft tissue 22, so as to define any geometric pattern as desired. In accordance with one embodiment as illustrated in FIG. 1, the soft tissue fixation assembly 20 can include a third bone anchor 26c driven through the soft tissue 22 and the bone 24, and a fourth bone anchor 26d driven through the bone 24 at a location spaced from both the soft tissue 22 and the first bone anchor 26a. The strand of suture 28 can extend continuously from each of the plurality of bone anchors 26 to at least one adjacent one of the plurality of bone anchors 26. Thus, the plurality of bone anchors 26 can define at least one row 32, such as a first row 32a that can be defined by at least some of the plurality of bone anchors 26, and a second row 32b that can be defined by at least others of the plurality of bone anchors 26, the strand of suture 28 connected between the first and second rows 32a and 32b. The rows 32a and 32b can extend substantially linearly, curvilinearly, or can define any other suitable arrangement, and can be parallel with each other or aligned to intersect each other as desired. The fixation assembly 20 can define as many rows as desired.

Referring now to FIGS. 2A-2E, each of the bone anchors 26 can include an anchor body 34 that defines a proximal end 36a and a distal end 36b that is spaced from the proximal end 36a along a distal direction of insertion into bone. It should be appreciated that the term "distal" and derivatives thereof can refer to a direction from the proximal end 36a to the distal end 36b, and the term "proximal" and derivatives thereof can refer to a direction from the distal end 36b to the proximal end 36a. The anchor body 34 can extend, for instance can be elongate, along a longitudinal axis 38, such that the proximal end 36 and distal end 36b are spaced from each other along the longitudinal axis 38. The longitudinal axis 38 can be substantially straight, or can be curved or assume any alternative shape as desired. The anchor body 34 can further define an outer perimeter 40 extends between the proximal end 36a and the distal end 36b. The perimeter 40 can be round, for instance substantially circular, as illustrated, or can define any alternative shape whatsoever, such as a rectilinear shape. The distal end 36b can define a tip 37 that can be tapered inwardly, and thus toward the longitudinal axis 38, as it extends along the distal direction.

The anchor body 34 can further define at least one channel 42, such as a plurality of (e.g., at least two) channels 42, that extend into the perimeter 40, for instance toward the longitudinal axis 38. Each of the channels 42 can be configured to receive the strand of suture 28 (see FIGS. 4A-B). For instance, respective ones of the channels 42 are configured to receive respective portions of the strand of suture 28. Each channel 42 can define a central axis 43a, and a first or proximal end 43b, and a second or distal end 43c that is spaced from the proximal end 43b along the central axis 43a. The channels 42 can extend along an entirety of the length of the anchor body 34 from the proximal end 36a to the distal end 36b, or can extend along a portion of the length of the anchor body 34. Thus, it can be said that the channels 42 can extend between the proximal and distal ends 43b and 43c, respectively, for instance from the proximal end 43b to the distal end 43c. The channels 42 can, for instance, be open to a proximal-most outer surface 54 of the anchor body 34, the proximal-most outer surface 54 extending from the outer perimeter 40 toward the longitudinal axis 38. The central axis 43a can extend parallel to the longitudinal axis 38, or can be angularly offset with respect to the longitudinal axis 38, and can define any shape as desired. The anchor body 34 can include any number of channels 42, such as a first channel 42a and a second channel 42b, that can be disposed on opposite sides with respect to the longitudinal axis 38, and thus be opposite each other with respect to the longitudinal axis 38, or can be angularly offset with respect to the longitudinal axis 38 at any angle of separation as desired.

Thus, a first line 35a perpendicular to the longitudinal axis 38 that intersects both the longitudinal axis 38 and the central axis 43a of the first channel 42a can define the angle of separation with respect to a second line 35b that is perpendicular to the longitudinal axis 38 and intersects both the longitudinal axis 38 and the central axis 43a of the second channel 42b. The angle of separation α1 can be substantially 180 degrees, or any angle between zero and 180 degrees. In accordance with the illustrated embodiment, the anchor body 34 can include a third channel 42c and a fourth channel 42d that can define an angle of separation with respect to each other, for instance 180 degrees as described above with respect to the first and second channels 42a and 42b. Further, the channels 42 can be equidistantly spaced from each other about the perimeter 40 as illustrated, or can be variably spaced from each other about the perimeter 40 as desired. Thus, adjacent ones of the channels 42, such as the first channel 42a and either or both of the third and fourth channels 43c and 43d, respectively, can define an angle of separation α2 of substantially 90 degrees. The channels 42 that are spaced from each other by an angle of separation that is greater than 90 degrees and less than or equal to 180 degrees can be referred to as opposed channels. The channels 42 that are spaced from each other by an angle of separation that is greater than between 0 degrees and less than or equal to 90 degrees can be referred to as adjacent channels.

As will be appreciated from the description below, at least a portion up to all of the anchor body 34 can be made from a deformation material 44, which can be polymeric, that comprises a deformation material responsive to an applied energy that causes the deformation material, and thus the anchor body 34 at the deformation material, to deform. The applied energy can be a laser or any suitable alternative energy, such as an electrical current. In accordance with one embodiment, the deformation material 44 can define at least a portion of the anchor body 34, including at least a portion up to an entirety of one or more up to all of the channels 42. For instance, the deformation material 44 can be located in a region as illustrated in FIGS. 3A-C that can be spaced from one or both of the proximal end 36a and the distal end 36b. Alternatively, the deformation material 44 can comprise an entirety of the anchor body 34, from the proximal end 36a to the distal end 36b, as illustrated in FIGS. 2A-2E. The deformation material 44 can be responsive to the applied energy so as to deform at least a portion of the anchor body 34 and capture the received portion of the strand of suture 28 therein with respect to movement relative to the anchor body 34. Deformation of the deformation material 44 in response to the applied energy can further cause the anchor body 34 to similarly deform and become fixed to the bone 24. In accordance with one embodiment, the deformation that causes the anchor body 34 to become fixed to the bone can similarly cause the anchor body 34 to capture the received portion of the suture strand 28 therein with respect to movement relative to the anchor body 34.

For instance, in accordance with one embodiment, the deformation material 44 is configured to deform in response to the applied energy and close at least a portion of each of the channels 42 and capture the respective received portion of the strand of suture 28 in the channels 42 with respect to movement relative to the anchor body 34. Deformation of the deformation material 44 in response to the applied energy can further cause the anchor body 34 to similarly deform and become fixed to the bone 24. In accordance with one embodiment, the deformation that causes the anchor body 34 to become fixed to the bone can similarly cause the channels 42 to close and capture the received strand of suture 28 therein. In accordance with one embodiment, the deformation material 44 can be disposed in a middle region of the anchor body 34 that is spaced from the proximal end 36a and the distal end 36b. For instance, the middle region can include a location that is disposed midway between the proximal end 36a and the distal ends 36b. The bone anchor body 34 can be constructed so as to prevent the applied energy from traveling to the distal end 36b. For instance, the bone anchor body 34 can define any color as desired, or be made of any one or more suitable materials as desired, that can prevent the applied energy from traveling to at least one select region of the bone anchor body 45, such as the distal end 36b. Examples of deformation materials of the type described herein are disclosed in U.S. Patent Application Publication No. 2010/0241229 A1, published Sep. 23, 2010, and U.S. Patent Application Publication No. 2012/0129131 A1, published May 24, 2012, the disclosure of each of which is incorporated by reference as if set forth in its entirety herein.

As described above, each of the channels 42 can define a central axis 43a, and a first or proximal end 43b, and a second or distal end 43c that is spaced from the proximal end 43b along the central axis 43a. In accordance with one embodiment, the distal ends 43c of the channels 42 can be open to each other, such that the strand of suture 28 can extend distally along one of the channels 42 out the distal end 43c of the channel, into the distal end 43c of another one of the channels 42 and proximally along the other one of the channels 42. For instance, the distal ends 43c of the channels 42 can be open to each other at the distal end 36b of the anchor body 34. In accordance with one embodiment, the anchor body 34 can define a void 46 that extends along the proximal direction into the tip 37. The void 46 can be aligned with the longitudinal axis 38, and can be open to the distal ends 43c of each of the channels 42, including the first channel 42a, the second channel 42b, the third channel 42c, and the fourth channel 42d. While the void 46 is open through the tip 37 along the distal direction as illustrated, it should be appreciated that the tip 37 can alternatively be enclosed, such that the tip 37 defines a distal boundary of the void 46. Nevertheless, the void 46 can be open to the outer perimeter 40 and to each of the distal ends 43c of the channels 42.

Thus, the distal ends 43c of each of the third and fourth channels 42c and 42d are open to both each other and the distal ends 43c of the first and second channels 42a and 42b, for instance at the distal end 36b. Similarly, the distal ends 43c of each of the first and second channels 42a and 42b are open to both each other and the distal ends 43c of the third and fourth channels 42c and 42d, for instance at the distal end 36b. For instance, the distal ends 43c can be open to each other via the void 46, such that strands of suture extending from the distal end 43c of one of the channels 42 to the distal end 43c of another one of the channels 42 can extend across the void 46. Alternatively, the distal ends 43c of one or more up to all of the channels 42 can be continuous with each other.

Each channel 42 can be defined by at least one wall that can define a base 45a of the anchor body 34 and opposed side walls 45b of the anchor body 34 that extend from the base 45a toward, for instance to, the perimeter 40. The void 46 can be at least partially defined by a floor 51 that extends toward the perimeter 40, and the anchor body 34 can define respective interface 49 between the bases 45a and the floor 51. The interface 49 can be beveled as desired.

With continuing reference to FIGS. 2A-E, the anchor 26 can define an insertion aperture 52 that extends into the anchor body 34 and is configured to receive an energy emitting instrument 70 (see FIG. 5A) that is configured to apply the energy that causes the deformation material 44 to deform as described herein. For instance, the anchor body 34 can define the insertion aperture 52 that extends into the proximal end 36a, and in particular the proximal-most surface 54, substantially along the distal direction. For instance, the insertion aperture 52 can be centrally disposed with respect to the outer perimeter and the longitudinal axis 38, and thus can extend substantially along the longitudinal axis 38. As will be described in more detail below, the insertion aperture 52 can be sized to receive an energy emitting instrument 70 (see FIG. 5A) that is configured to apply the energy that causes the deformation material 44 to deform in the manner described herein. The insertion aperture 52 can be round, such as cylindrical, in shape, or can define any suitable alternative shape as desired. The insertion aperture 52 can be defined by a base 53a of the anchor body 34 and at least one inner side wall 53b that can extend from the base 53a along the proximal direction, for instance to the proximal outer surface 54 of the proximal end 36a. In accordance with one embodiment, the proximal end 36a that defines the insertion aperture 52 can be integral and monolithic with one or more up to all of the distal end 36b, the base 45a of one or more up to all of the channels 42, the side walls 45b of one or more up to all of the channels 42, the floor 51, and the interfaces 49.

Alternatively, as illustrated in FIGS. 3A-C, the bone anchor can include an insert 56 that defines an insert body 59 having a proximal end 56a, a distal end 56b spaced from the proximal end 56a along the distal direction, and an outer perimeter 56c that extends from the proximal end 56a to the distal end 56b. The insert 56 can define the insertion aperture 52 that is configured to receive the energy emitting instrument 70 (see FIG. 5A) that is configured to apply the energy to the deformation material 44. The bone anchor 26 can define an aperture 60 that extends into the anchor body 34 and is sized and configured to receive the insert 56. For instance, the body 34 can define the aperture 60 that extends into the proximal end 36a substantially along the distal direction. For instance, the insertion aperture 60 can be centrally disposed with respect to the outer perimeter and the longitudinal axis 38, and thus can extend substantially along the longitudinal axis 38. The insert 56 can be insertable in the aperture 60 in any manner as desired. For instance, the perimeter 56c of the insert 56 can define a cross-sectional dimension substantially equal to that of the aperture 60, such that the insert 56 can be press-fit into the aperture 60. Alternatively, the insert 56 can be secured to the anchor body 34 in the aperture 60 using any known adhesive, fastener, or the like. The insert 56 can define a head 61 that extends out from the proximal end 56a of the body 59 and is configured to abut the proximal most surface 54. The head 61 can define channels 57 that are aligned with the channels 42 and extend through the head 61 along the distal direction. Thus, the channels 42 and 57 can combine to define the respective channels that are configured to receive the strands of suture 28 as described herein. The insert 56 can be made from a material different than the deformation material, such that the insert 56 does not deform in response to application of the energy.

Figure 5A:
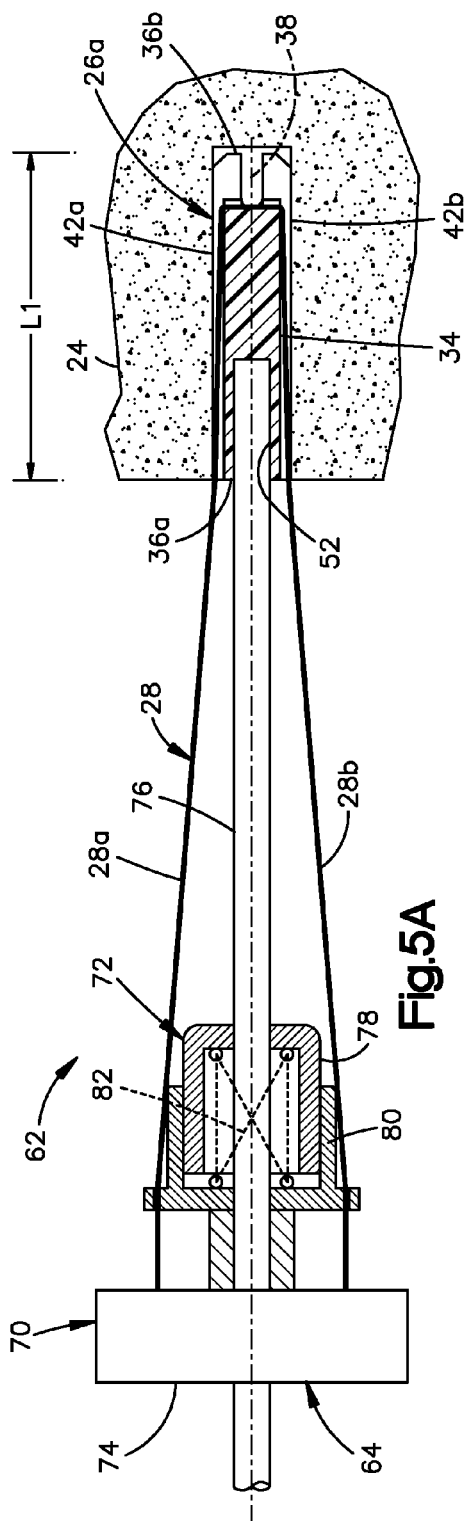
FIG. 5A is a schematic sectional side elevation view of a soft tissue fixation system constructed, including an actuation assembly shown operably engaged with an initial bone anchor of the soft tissue fixation assembly illustrated in FIG. 1.

Referring now to FIG. 5A, a soft tissue fixation system 62 can include an actuation assembly 64 and the soft tissue fixation assembly 20. The soft tissue fixation assembly 20 can include at least one bone anchor, such as a plurality (such as a pair or more) of bone anchors 26 and at least one strand of suture 28. The actuation assembly 64 can include the energy emitting instrument 70 and a tensioner 72 that supports the energy emitting instrument 70. The energy emitting instrument 70 is configured to apply energy to the anchor body 34, thereby causing the deformation material 44 to deform. As the deformation material 44 deforms, the tensioner 72 can maintain tension in the suture 28.

The energy emitting instrument 70 can include an energy source 74 and an energy conduit 76 that extends from the energy source 74 and is configured to be inserted into the insertion aperture 52 so as to be configured to apply energy to the implant body 34 in sufficient quantity that the deformation material 44 deforms in response to the applied energy, or can otherwise be operably coupled to the implant body 34 so as to be configured to apply energy to the implant body 34 in sufficient quantity that the deformation material 44 deforms in response to the applied energy. In accordance with the illustrated embodiment, the energy emitting instrument 70 is a laser, the energy source 74 is a laser source configured to emit energy in the form of a laser beam. The energy conduit 76 can define a light pipe that extends from the laser source, the light pipe configured to communicate the laser beam from the laser source to the implant 26, and apply the energy in the form of the laser beam to the implant body 34.

The tensioner 72 can include a first support member 78 configured to support the energy conduit 76, and a second support member 80 that is spaced from the first support member along a direction that can be parallel, such as coincident, with the longitudinal axis 38. In accordance with the illustrated embodiment, the second support member 80 can be spaced from the first support member 78 along the proximal direction, such that the first support member 78 is disposed between the second support member 80 and the bone anchor 26 that receives the energy conduit 76. The second support member 80 is configured to attach to the suture 28 that extends through at least one of the channels 42 of the bone anchor 26. The tensioner 72 can include a biasing member 82, for instance a spring such as a coil spring that is connected between the first and second support members 78 and 80, respectively. The tensioner 72 is configured to bias one of the first and second support members 78 and 80, respectively, to move relative to the other of the first and second support members 78 and 80, respectively.

During operation, the biasing member 82 applies a force to the second support member 80 that biases the second support member to move along the proximal direction away from the bone anchor 26, and also away from the first support member 78. Alternatively, the second support member 80 can be disposed distal of the first support member 78, and thus between the first support member 78 and the bone anchor 26, such that the biasing member 82 applies a force to the second support member 80 that biases the second support member 80 to move along the proximal direction away from the bone anchor 26 and toward the first support member 78.

With continuing reference to FIG. 5A, a method of anchoring suture to bone can include the step of inserting the strand of suture 28 into at least one channel 42 of an initial bone anchor, which can be defined as a first bone anchor 26. In particular, the strand of suture 28 can be inserted into first and second select ones of the channels 42, such that the strand of suture 28 extends from the proximal end 36a, distally along the first select one of the channels 42, out the distal end of the first select one of the channels 42 as described above, into the distal end of the second select one of the channels 42, proximally along the second select one of the channels 42, and out the proximal end 36a of the anchor body. The first and second select channels can be opposed channels or adjacent channels as described above.

After the strand of suture 28 has been inserted into the at least one channel 42, the bone anchor 26 can be driven into the bone 24. A pilot hole can be drilled or otherwise formed in the bone, and the initial anchor 26 can be driven into the pilot hole, or the anchor 26 can be driven into the bone without first forming the pilot hole. Next, the energy conduit 76 is inserted into the insertion aperture 52 or otherwise operably coupled to the anchor body 34. At least one end of the strand of suture 28, for instance first and second opposed ends 28a and 28b that extend out from different ones of the channels 42 of the initial bone anchor, can be fixedly attached to the second support member 80 prior to deformation of the initial bone anchor.

Figure 5B:
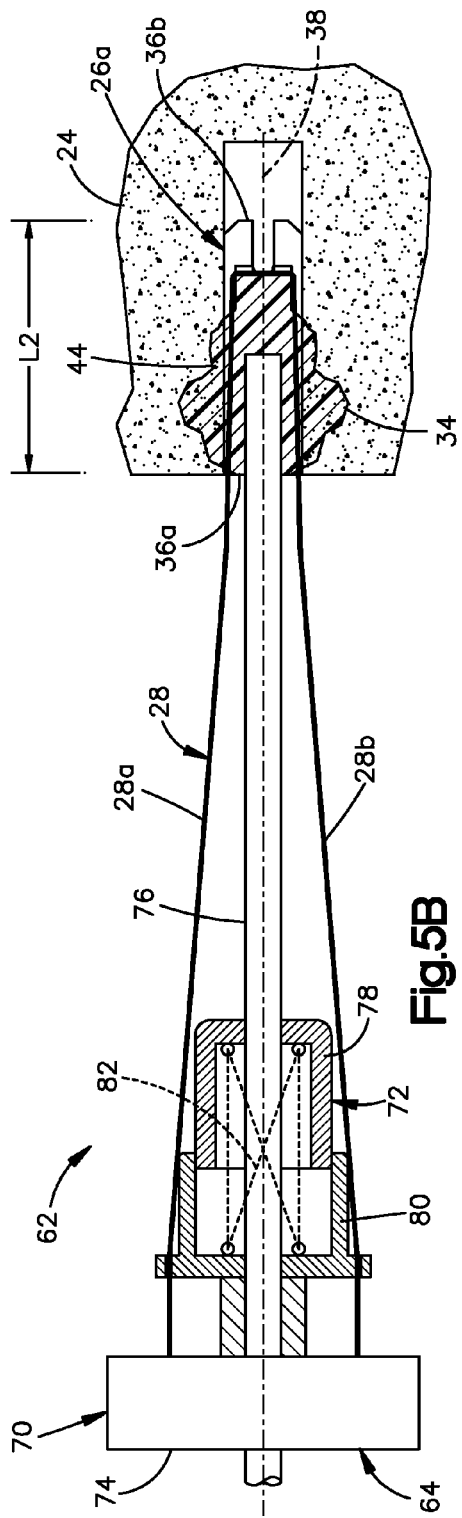
FIG. 5B is a schematic sectional side elevation view of the soft tissue fixation system illustrated in FIG. 5A, shown after activation of the actuation assembly.

Referring now to FIG. 5B, the energy source 74 is then actuated so as to cause the energy emitting instrument 70, for instance the energy source 74, to emit energy, which can be in the form of a laser beam, to the conduit 76. The energy emitting instrument, for instance at the conduit 76, can apply the energy to the bone anchor body 34 so as to cause the deformation material 44 to deform, thereby causing the anchor body to deform and 1) fix to the bone 24, and 2) capture the strand of suture 28 therein with respect to movement relative to the bone anchor 26. For instance, the energy emitting instrument, for instance at the conduit 76, can apply the energy to the bone anchor body 34 so as to cause the deformation material 44 to deform and close at least the portion of the channel 42 that is defined by the deformation material 44, thereby capturing the strand of suture 28 therein with respect to movement relative to the bone anchor 26. Thus, the strand of suture 28 is unable to move relative to the bone anchor 26 at the portion of the channel 42 that has been closed. In accordance with the illustrated embodiment, both channels within which the suture 28 resides can be closed.

It is appreciated that prior to deformation of the first bone anchor, the first bone anchor 26 defines a first length L1 along the longitudinal axis 38 between the proximal end 36a and the distal end 36b. As the deformation material 44 deforms, the distal end 36b can be drawn toward the proximal end 36a, thereby shortening the length of the bone anchor to a second length L2 along the longitudinal axis 38 between the proximal end 36a and the distal end 36b, wherein the second length L2 is less than L1. For instance, the biasing force of the biasing member 82 causes the second support member 80, which is attached to the suture 28, to translate proximally as the deformation material 44 of the anchor body 34 softens and deforms in response to the applied energy, thereby promoting deformation of the anchor body 34 as described above. Furthermore, translation of the second support member 80 can cause the first and second ends 28a and 28b to likewise translate proximately, thus maintaining a desired level of tension in the strand of suture 28 through completion of the application of energy to the anchor body 34 and through completion of the resulting deformation. It is further appreciated that a maximum width of the anchor body 34 along a direction perpendicular to the longitudinal axis 38 can increase in response to deformation of the deformation material 44, thereby securely anchoring the bone anchor in the bone 24. It should be appreciated, of course, that the biasing force can be produced by any suitably constructed tensioner 72, or manually, as desired.

Figure 5C:
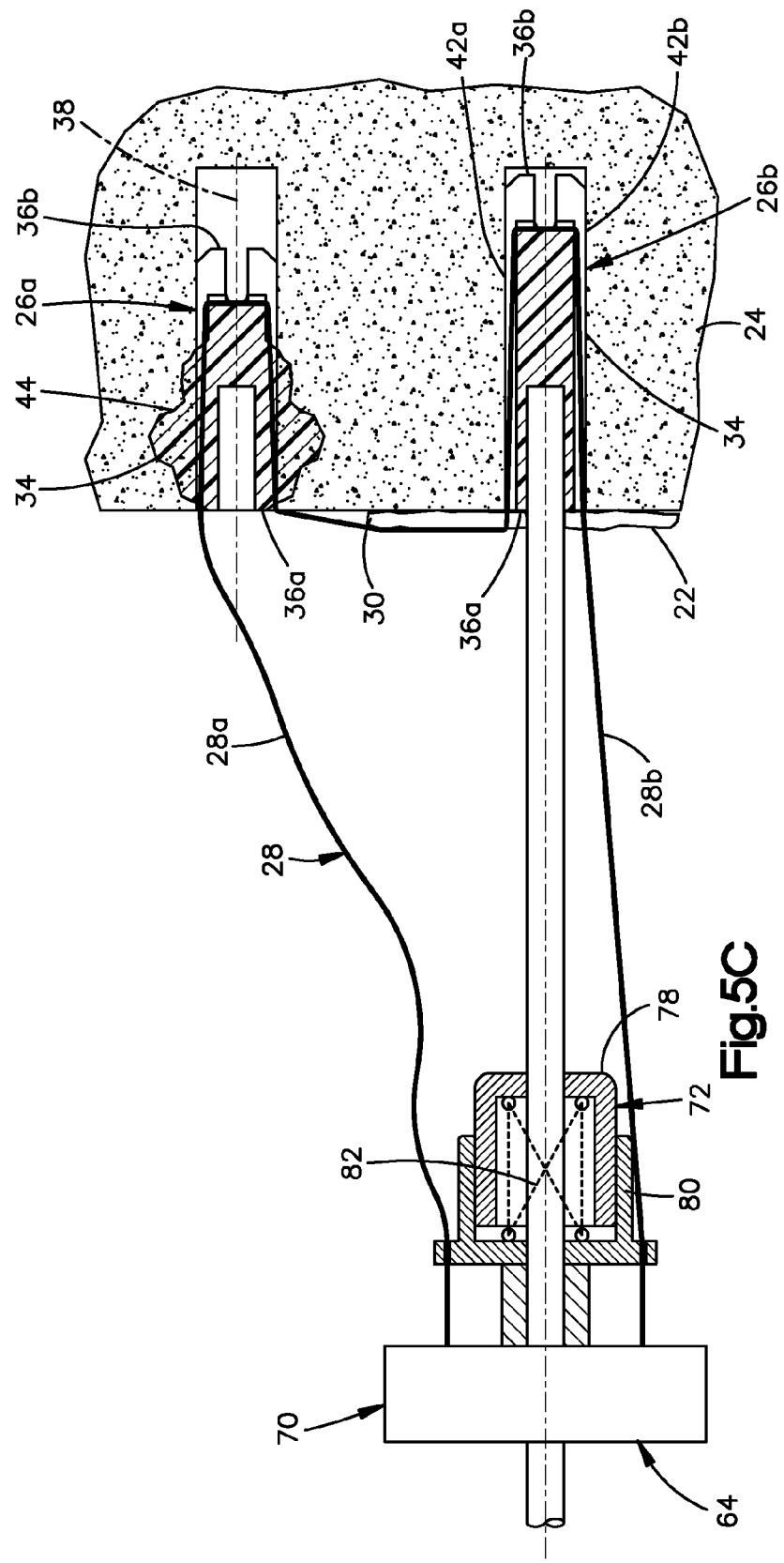
FIG. 5C is a schematic side elevation view of a soft tissue fixation system illustrated in FIG. 5B, showing the actuation assembly operably engaged with a subsequent bone anchor of the soft tissue fixation assembly illustrated in FIG. 1.

Referring now to FIG. 5C, it is appreciated that the first end 28a is fixed to the initial bone anchor. Accordingly, the first end 28a can be cut at a location adjacent to the proximal end 36a of the anchor body 34, or the first end 28a can define a free end of the strand of suture 28 that extends out from the bone 24. The free end can be loosely attached to the second support member 80, or can be free from the second support member 80. As is described in more detail below, the free end can be attached to a final one of the bone anchors 26. The second end 28b can then be inserted into first and second select channels of a subsequent bone anchor, which can be define as a second bone anchor 26b, in the manner described above with respect to the first anchor 26a. The first and second channels 42 can be opposed channels or adjacent channels as described above. The second end 28b can extend out the anchor body 34 and can be attached to the second support member 80 in the manner described above.

After the strand of suture 28 has been inserted into the channels 42 of the second bone anchor 26b, the second bone anchor 26b can be driven into the bone 24 in the manner described above. It should be appreciated that the second bone anchor 26 can be driven through the soft tissue 22 and into the bone 24. Next, as illustrated in FIG. 5D, the method can include the step of applying energy to the second bone anchor 26b so as to cause the deformation material 44 of the second bone anchor 26b to deform, thereby capturing the strand of suture 28 therein with respect to movement relative to the second bone anchor 26b. For instance, deforming the deformation material 44 can close the portion of the channels 42 that is defined by the deformation material 44, thereby capturing the received strand of suture 28 therein with respect to movement relative to the second bone anchor 26b. The biasing member 82 can apply a biasing force to the second support member 80 that causes the second support member 80 to move away from both the first support member 78 and the first and second bone anchors 26a and 26b, thereby promoting deformation and maintaining tension in the strand of suture 28 as the length of the second bone anchor 26b decreases in the manner described above with respect to the first bone anchor 26a. It should be appreciated that the strand of suture 28 is continuous, and is fixedly attached to the first and second bone anchors 26a and 26b. Thus, the strand of suture 28 extends continuously from the first bone anchor 26a, over the bone 24, across the interface 30 between the soft tissue 22 and the bone 24, over the soft tissue 22, to the second bone anchor 26b. Because the strand of suture 28 is in tension and is anchored to the first and second bone anchors 26a and 26b inside the bone 24, the strand of suture 28 forces the soft tissue 22 into contact with the bone 24.

Figure 6A:
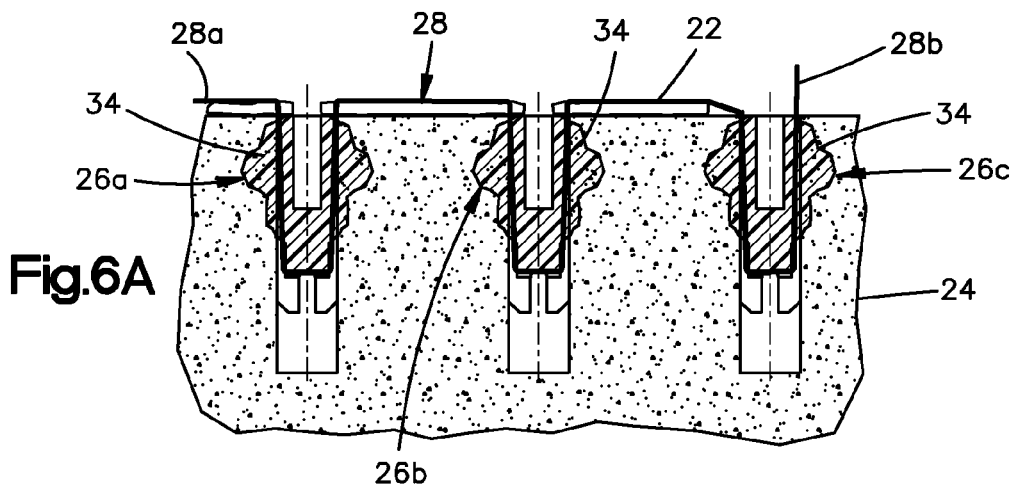
FIG. 6A is a schematic sectional side elevation view of a portion of the bone fixation assembly 1, showing a single strand of suture sequentially connected continuously to a plurality of the bone anchors.

It should be appreciated that the method steps of inserting the strand of suture 28 into at least one such as a pair of channels, driving the bone anchor into the bone, for instance possibly through the soft tissue 22 and into the bone 24, and applying the energy to the anchor body can be sequentially repeated for at least one additional bone anchor, such a third bone anchor 26c as illustrated in FIG. 6A. For instance, the method steps of inserting the strand of suture 28 into at least one such as a pair of channels, driving the bone anchor into the bone, for instance possibly through the soft tissue 22 and into the bone 24, and applying the energy to the anchor body can be sequentially repeated for a plurality of additional bone anchors 26c. In accordance with one embodiment, the energy is applied to a given one of the bone anchors 26 prior to inserting the strand of suture 28 into a channel 42 of another one of the bone anchors 26 that is to be subsequently anchored to the bone 24.

Figure 6B:
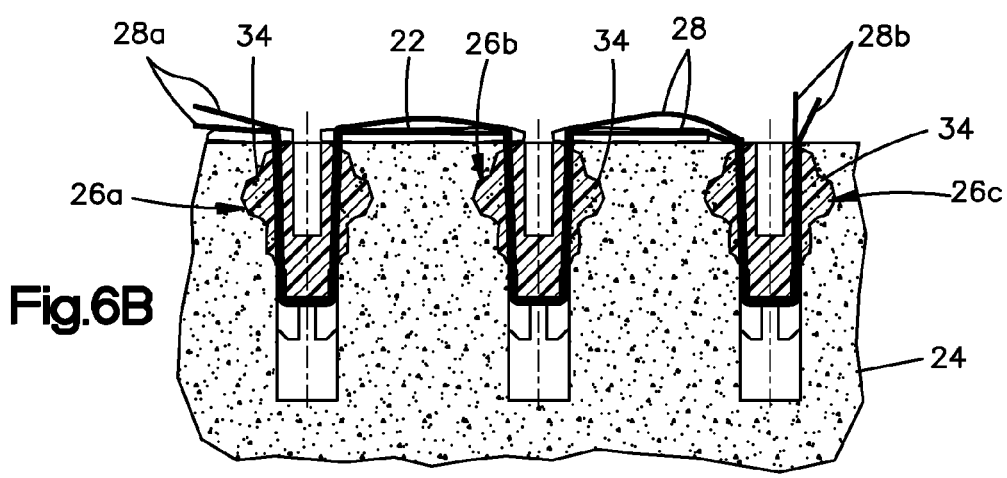
FIG. 6B is a schematic sectional side elevation view of a portion of the bone fixation assembly 1, showing a pair of strands of suture each sequentially connected continuously to a plurality of the bone anchors.
Figure 6C:
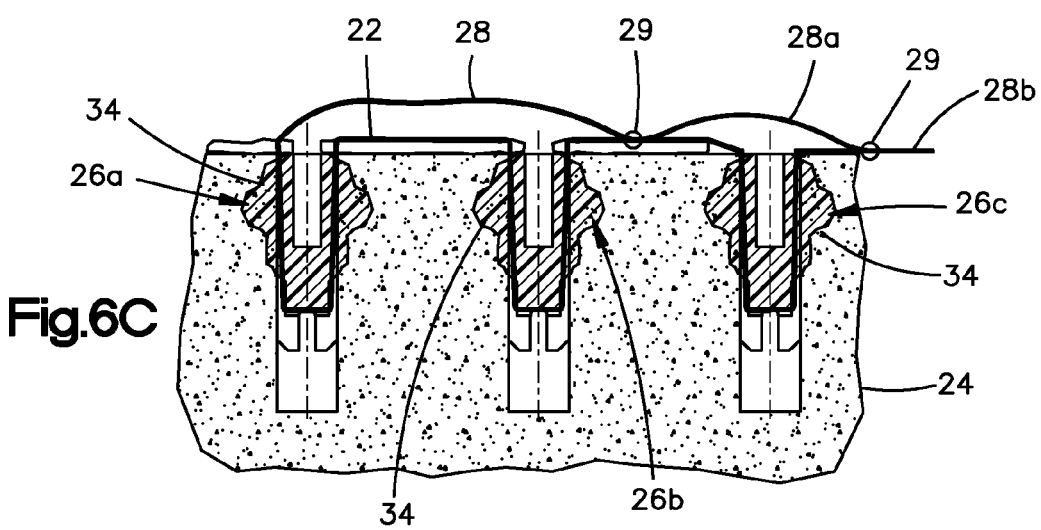
FIG. 6C is a schematic sectional side elevation view of a portion of the bone fixation assembly 1, showing the pair of strands of suture each sequentially connected continuously to a plurality of the bone anchors, one of the strands of suture configured to attach to an auxiliary implant.

As described above, at least one strand of suture can be inserted into the channels 42 of the anchors 26 prior to driving the anchors into bone and applying the energy to the respective anchor bodies 34. For instance, as illustrated in FIG. 6A, a single continuous strand of suture 28 can be fixedly attached sequentially to at least two, such as three, bone anchors 26a, 26b, and 26c. Alternatively, as illustrated in FIG. 6B, it should be appreciated that the steps of inserting a strand of suture into at least one channel of the bone anchors 26 can include the step of inserting a pair or more, and thus a plurality, of strands of suture 28 into the at least one channel. Accordingly, the step of applying energy to the implant body causes the anchor body, and thus the anchor, to deform so as to secure each of the plurality of strands of suture 28 to the respective anchor body. Deformation of the anchor body can further cause the anchor body to fix to the bone 24, and can cause the portion of the channels defined by the deformation material to close so as to secure the strands of suture 28 therein with respect to movement relative to the anchor body. A free end of the single strand of suture 28, or of a second strand of suture 28, can extend out the proximal end of the bone anchor 26, and out the bone 24, such that it can be attached to an auxiliary implant, such as a soft tissue or bone graft, and then secured to itself or the other strand of suture 28, for instance at a knot 29, thereby attaching the auxiliary implant to the soft tissue 22 or bone 24.

Figure 7D:
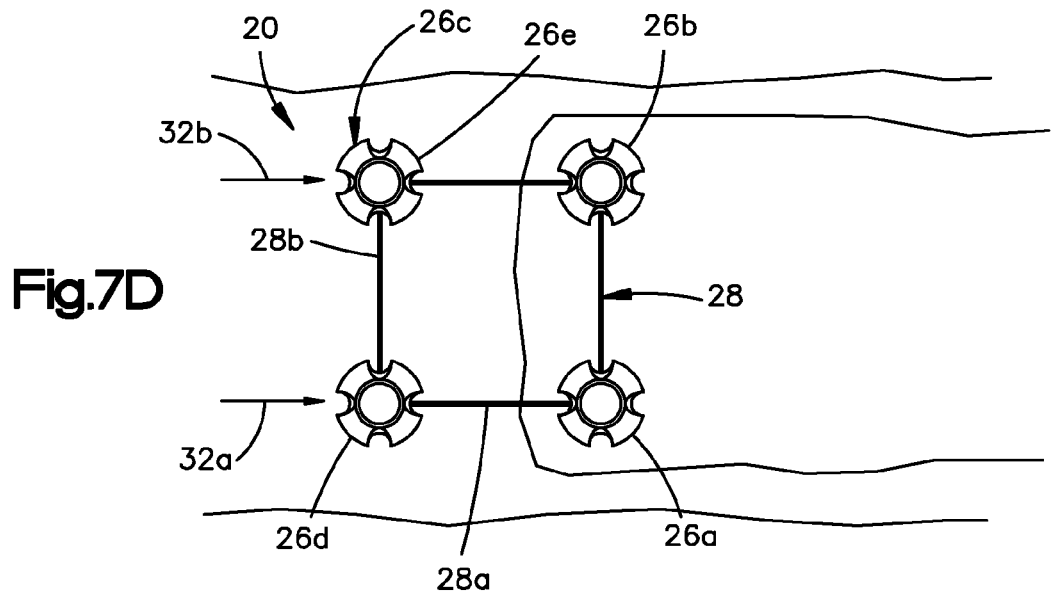
FIG. 7D is a schematic plan view of the soft tissue fixation assembly as illustrated in FIG. 7C, but showing the bone anchors in a closed arrangement in accordance with another embodiment.

Referring now to FIGS. 7A-7E in general, it is appreciated that the soft tissue fixation assembly 20 can include as many bone anchors 26 as desired, disposed in any arrangement as desired. For instance, as illustrated in FIG. 7A, the first bone anchor 26a is shown inserted into the bone without being driven through the soft tissue 22, and the second one anchor 26b is shown inserted through the soft tissue 22 and into the bone 24. The first and second bone anchors 26a and 26b can define a row 32 of bone anchors. Referring to FIG. 7B, the plurality of bone anchors 26c, in combination with the first and second bone anchors 26a and 26b can define a pair of rows, such as a first row 32a and a second row 32b. For instance, the row defined by the first and second bone anchors 26a and 26b can define the first row 32a, and the plurality of bone anchors 26c can define the second row 32b that is adjacent the first row 32a. The strand of suture 28 can extend from the first row 32a to the second row 32b. For instance, the strand of suture 28 can extend through adjacent channels 42 (see FIG. 2D) of one of the bone anchors, such as the second bone anchor 26b illustrated in FIG. 7B, so as to extend from the first row 32a along a column direction toward the second row 32b. The strand of suture 28 can then extend through adjacent channels of a subsequent one of the bone anchors, such as one of the plurality of bone anchors 26c illustrated in FIG. 7B, so as to extend from the column direction to the row direction, for instance along the second row 32b.

With continuing reference to FIG. 7B, the step of driving a final bone anchor 26d of the plurality of bone anchors 26c can include the step of driving the final bone anchor 26d into the bone 24 at a location spaced from the first bone anchor 26a. Thus, the strand of suture 28 is not connected directly from the final bone anchor 26d to the first bone anchor 26a. Because the strand of suture 28 is not directly connected between the bone anchors 26 of every adjacent pair of bone anchors 26, the arrangement defined by the bone anchors 26 can be referred to as an open arrangement. As described above, the soft tissue fixation assembly 20 can include as many bone anchors as desired, configured in any arrangement as desired. For instance, the soft tissue fixation assembly 20 can define as many rows 32 as desired.

Figure 7E:
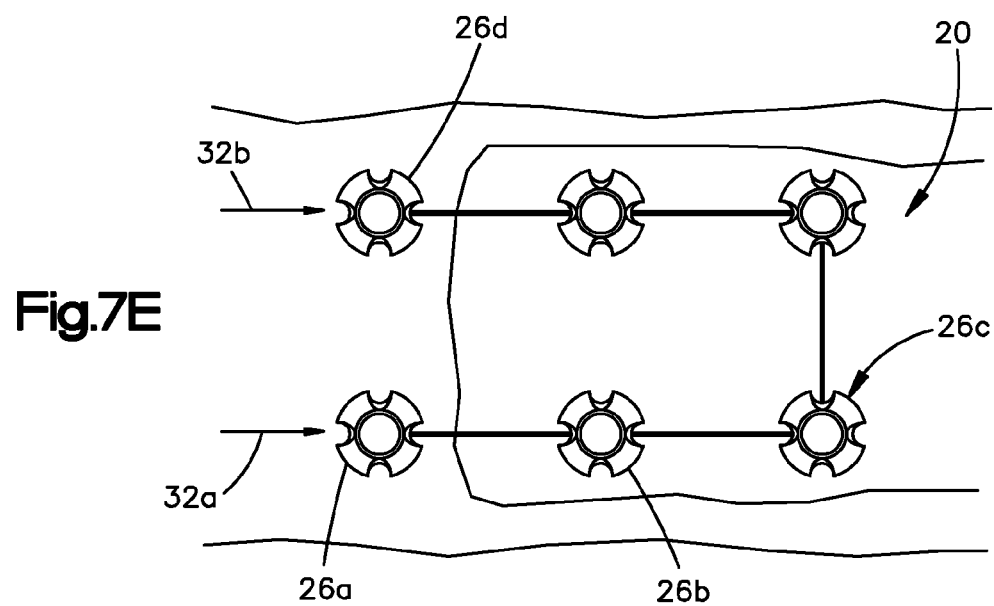
FIG. 7E is a schematic plan view of the soft tissue fixation assembly as illustrated in FIG. 7B, but showing the bone anchors in an open arrangement in accordance with another embodiment.

Referring to FIG. 7E, the suture 28 of the soft tissue fixation assembly 20 can extend from the second bone anchor 26b to a first one of the plurality of bone anchors 26c along the first row 32a. In accordance with one embodiment, the strand of suture 28 can be inserted into opposed channels of the second bone anchor 26b, wherein the opposed channels are spaced from each other along a direction that is substantially parallel with the row 32a. The suture 28 can extend from the second bone anchor 26b toward a first one of the plurality of bone anchors 26c. The strand of suture 28 can be inserted into adjacent columns of the first one of the plurality of bone anchors 26c. Thus, the suture 28 can extend from the second bone anchor 26b along the row 32a to the first one of the plurality of bone anchors 26c, and along a column direction from the first one of the plurality of bone anchors 26c to a second one of the plurality of bone anchors 26c that lies along the second row 32b. The strand of suture 28 can be inserted into adjacent columns of the second one of the plurality of bone anchors 26c so as to extend from the first one of the plurality of bone anchors 26c to the second one of the plurality of bone anchors 26c along the column direction, and along the second row 32b from the second one of the plurality of bone anchors 26c to another one of the plurality of bone anchors.

Of course, it should be appreciated that the strand of suture 28 can be inserted into any channels of the bone anchor 26 as desired so as to extend along a respective row 32, or to extend from a respective row along the column direction, or to extend from a column direction to a respective row. It should be further appreciated that the soft tissue fixation assembly 20 can define as many bone anchors as desired arranged along a given column direction. It should be further appreciated still that the soft tissue fixation assembly 20 can define a chain configuration having a plurality of rows of bone anchors 26, each row defined by two or more bone anchors 26, and the rows of adjacent pairs of rows (thus rows that are partially defined by a common one of the anchors 26) angularly offset from each other at an angle between 90 degrees and 180 degrees, or alternatively between 0 degrees and 90 degrees (and thus an angle other than 90 degrees). Thus, the first anchor 26a can be disposed at a first terminal end of the chain, and the final bone anchor 26d can be disposed at a second terminal end of the chain.

Referring now to FIG. 7C, the suture 28 can be connected between the final bone anchor 26d and the first bone anchor 26a. For instance, as described above with reference to FIG. 5C, the first end 28a of the strand of suture 28 can define a free end that extends out from the first bone anchor 26a and the bone 24. Similarly, the second end 28b of the strand of suture 28 can define a free end that extends out from the final bone anchor 26d and the bone 24. The free ends that are defined by the first and second ends 28a and 28b can be attached to each other in accordance with any suitable embodiment, so as to directly attach the suture 28 to the last bone anchor 26d and the first bone anchor 26a. For instance, the free ends can be tied to each other, or secure to each other via any suitable fastener. Because the strand of suture 28 is directly connected between the bone anchors 26 of every adjacent pair of bone anchors 26, the arrangement defined by the bone anchors 26 can be referred to as a closed arrangement.

Referring now to FIG. 7D, the bone anchors 26 can define a closed arrangement in accordance with an alternative embodiment. For instance, the plurality of additional bone anchors 26c can define a select bone anchor 26e that is driven into the bone 24 and deformed before the final bone anchor 26d is driven into the bone. As described above, the first end 28a of the strand of suture 28 can define a free end that extends out from the first bone anchor 26a and the bone 24 as described above. Furthermore, the second end 28b of the strand of suture 28 can define a free end that extends out from the select bone anchor 26e and the bone 24.

The free end defined by the first end 28a of the strand of suture 28 can be inserted into at least one channel of the final bone anchor 26d. For instance, the free end defined by the first end 28a of the strand of suture 28 can be inserted into a first channel 42 of the final bone anchor 26d, and out of a second channel 42 of the final bone anchor 26d. The first and second channels of the final bone anchor 26d can be adjacent channels or opposed channels as described above. Similarly, the free end defined by the second end 28b of the strand of suture 28 can be inserted into at least one channel of the final bone anchor 26d. For instance, the free end defined by the second end 28b of the strand of suture 28 can be inserted into a first channel 42 of the final bone anchor 26d, and out of a second channel 42 of the final bone anchor 26d. The first and second channels can be adjacent channels or opposed channels as described above. In accordance with one embodiment, the first channel of the free end that receives the first end 28a can define the second channel that receives free end defined by the second end 28b. Similarly, the first channel that receives second end 28b can define the first channel that receives the first end 28a. It should be appreciated, of course, that the free ends defined by the first and second ends 28a and 28b, respectively, can be inserted into different channels of the final bone anchor 28d. In accordance with the embodiment illustrated in FIG. 2D, the first and second bone anchors 26a and 26b can each be driven through the soft tissue 22 and into the bone 24, and the select and final ones 26e and 26d, respectively, of the plurality of bone anchors 26c can be inserted into the bone 24 without being driven through the soft tissue 22.

The foregoing description is provided for the purpose of explanation and is not to be construed as limiting the soft tissue fixation system, or components thereof. While various embodiments have been described with reference to preferred embodiments or preferred methods, it is understood that the words which have been used herein are words of description and illustration, rather than words of limitation. Furthermore, although the embodiments have been described herein with reference to particular structure, methods, and embodiments, the disclosure is not intended to be limited to the embodiments specifically described herein. For instance, it should be appreciated that structure and methods described in association with one embodiment are equally applicable to all other embodiments described herein unless otherwise indicated. Those skilled in the relevant art, having the benefit of the teachings of this disclosure, may effect numerous modifications to the embodiments as described herein, and changes may be made without departing from the scope of the present invention, for instance as set forth by the appended claims.

What is claimed:

1. A bone anchor configured to deform in response to an applied energy from a laser, the bone anchor comprising:
    a bone anchor body having (1) a proximal end, (2) a distal end that is spaced from the proximal end along a central longitudinal axis, and (3) a perimeter surface that is unthreaded as it extends from the proximal end to the distal end, the bone anchor body defining first, second, third, and fourth channels that extend into the perimeter surface and are elongate as they extend between the proximal end and the distal end, the first channel spaced opposite the second channel along a first direction, and the third channel spaced opposite the fourth channel along a second direction that is perpendicular to the first direction,
    wherein at least a portion of the bone anchor body comprises a deformation material that defines at least a portion of the perimeter surface and each of the first, second, third, and fourth channels, the deformation material being responsive to the applied energy from the laser so as to deform and capture a strand of suture with respect to movement relative to the bone anchor body when the strand of suture is received by at least one of the first, second, third, and fourth channels, and the deformation material configured to prevent the applied energy from the laser from traveling to the distal end.

2. The bone anchor as recited in claim 1, wherein the first and second channels are configured to receive first and second portions, respectively, of the strand of suture, wherein the deformation material is responsive to the applied energy so as to deform and, when the first and second portions of the strand of suture are received in the first and second channels, respectively, capture the first and second portions of the strand of suture with respect to movement relative to the bone anchor body.

3. The bone anchor as recited in claim 2, wherein the deformation material is responsive to the applied energy so as to deform at least a portion of each of the first and second channels and, when the first and second portions of the strand of suture are received in the first and second channels, respectively, close at least a portion of each of the first and second channels and capture the first and second portions of the strand of suture therein with respect to movement relative to the bone anchor body.

4. The bone anchor as recited in claim 1, wherein the deformation material is disposed in a middle region of the anchor body that includes a location midway between the proximal and distal ends.

5. The bone anchor as recited in claim 1, wherein each of the first and second channels defines a first end, and a second end that is distal from the first end, and the second ends of the first and second channels are open to each other.

6. The bone anchor as recited in claim 5, wherein the second ends are open to each other at the distal end of the bone anchor body.

7. The bone anchor as recited in claim 5, wherein the third and fourth channels each define a first end, and a second end that is distal from the first end, and the second ends of the third and fourth channels are open to both (i) each other and (ii) the second ends of the first and second channels at the distal end.

8. The bone anchor as recited in claim 1, wherein the first and second channels each extend from the proximal end to the distal end.

9. The bone anchor as recited in claim 1, wherein the first and second channels are disposed on opposite sides with respect to the central longitudinal axis.

10. The bone anchor as recited in claim 1, wherein the first, second, third, and fourth channels are equidistantly spaced from each other about the perimeter surface.

11. The bone anchor as recited in claim 10, wherein the bone anchor body defines an aperture that extends into the proximal end, the bone anchor further comprising an insert that is insertable into the aperture, the insert defining an aperture that is configured to receive an energy emitting instrument that is configured to apply the energy to the deformation material.

12. The bone anchor as recited in claim 1, wherein the bone anchor body defines an aperture that extends into the proximal end substantially along the central longitudinal axis, the aperture configured to receive an instrument that applies the energy to the deformation material.

13. The bone anchor as recited in claim 12, wherein the proximal end that defines the aperture is integral and monolithic with the distal end.

14. The bone anchor as recited in claim 1, wherein each of the first, second, third, and fourth channels extends into the perimeter surface toward the central longitudinal axis.

15. The bone anchor of claim 1, wherein the bone anchor body defines a void that extends into a distal-most surface of the bone anchor body along the central longitudinal axis, and wherein the first, second, third, and fourth channels each define distal ends that are open to one another and the void.

16. The bone anchor of claim 15, wherein the bone anchor body has first and second internal surfaces that face one another so as to at least partially define the void, and the first and second internal surfaces are planar as they extend from the distal-most surface of the bone anchor to a floor of the void.

17. The bone anchor of claim 1, wherein each of the first to fourth channels extends through a proximal-most surface of the bone anchor.

18. The bone anchor of claim 1, wherein the bone anchor body includes a proximal-most surface having a maximum cross-sectional dimension that is equal to a maximum cross-sectional dimension of a middle region of the bone anchor.

19. The bone anchor of claim 1, wherein the deformation material defines a color that is configured to prevent the applied energy from the laser from traveling to the distal end.

20. A soft tissue fixation system comprising:
at least first and second bone anchors, each having (1) a proximal end, (2) a distal end that is spaced from the proximal end along a central longitudinal axis, (3) an outer perimeter surface that is unthreaded as it extends from the proximal end to the distal end, and (4) an internal surface that defines an aperture that extends into the proximal end substantially along the central longitudinal axis, the first and second bone anchors each defining first, second, third, and fourth channels, wherein (i) the first to fourth channels of the first bone anchor extend into the outer perimeter surface of the first bone anchor and are elongate as they extend between the proximal and distal ends of the first bone anchor, (ii) the first to fourth channels of the second bone anchor extend into the outer perimeter surface of the second bone anchor and are elongate as they extend between the proximal and distal ends of the second bone anchor, (iii) the first and second channels of each of the first and second bone anchors are spaced opposite one another along a first direction, and (iv) the third and fourth channels of each of the first and second bone anchors are spaced opposite one another along a second direction, perpendicular to the first direction;
a strand of suture sized to be received by each of the first and second bone anchors; and
an energy emitting instrument comprising a laser instrument including a laser source and a light pipe extending from the laser source, the light pipe configured to be received in the aperture of each of the first and second bone anchors and configured to carry a laser beam emitted by the laser source, and apply the laser beam to the each of the first and second bone anchors,
wherein (i) at least a portion of each of the first and second bone anchors comprises a deformation material that defines at least a portion of each of the first to fourth channels of the first and second bone anchors, respectively, (ii) the deformation material of the first and second bone anchors is responsive to an applied energy so as to deform and, when the suture is received by the first and second bone anchors, capture the strand of suture in the first and second bone anchors with respect to movement relative to the first and second bone anchors, and (iii) the deformation material of each of the first and second bone anchors defines a color configured to prevent the laser beam from the laser from traveling to the distal ends of the first and second bone anchors.

21. The soft tissue fixation system as recited in claim 20, wherein the first and second channels of the first and second bone anchors are each configured to receive the strand of suture, and the deformation material of the first and second bone anchors is responsive to the applied energy so as to deform and close each of the first and second channels of the first and second bone anchors, thereby capturing the strand of suture in each of the first and second channels of the first and second bone anchors when the suture is received in each of the first and second channels of the first and second bone anchors.

22. The soft tissue fixation system as recited in claim 20, wherein the first and second channels of the first bone anchor extend toward the central longitudinal axis of the first bone anchor and the first and second channels of the second bone anchor extend toward the central longitudinal axis of the second bone anchor.

23. The soft tissue fixation system as recited in claim 20, further comprising a first support member configured to support the light pipe, and a second support member configured to attach to at least one end of the strand of suture.

24. The soft tissue fixation system as recited in claim 23, further comprising a biasing element coupled between the first and second support members, the biasing element biasing the second support member to move away from the first and second bone anchors so as to apply a compressive force onto a respective one of the first and second bone anchors that is receiving the applied energy.

25. The soft tissue fixation system as recited in claim 24, wherein the biasing member comprises a spring that biases the second support member to move away from both the first support member and the first and second bone anchors.

26. The soft tissue fixation system as recited in claim 23, wherein the second support member is configured to attach to a first end of the strand of suture on a first side of the light pipe, and to a second end of the strand of suture on a second side of the light pipe, opposite the first side.

27. The soft tissue fixation system as recited in claim 23, wherein the first and second support members are spaced from one another along a longitudinal direction that is parallel to the central longitudinal axis, and the system comprises a biasing element that extends from the first support member to the second support member.

* * * * *